(12) United States Patent
Stoddard et al.

(10) Patent No.: US 6,319,699 B1
(45) Date of Patent: Nov. 20, 2001

(54) BACTERIAL STRAINS AND USE THEREOF IN FERMENTATION PROCESSES FOR 2-KETO-L-GULONIC ACID PROTECTION

(76) Inventors: Steven F. Stoddard, 111 S. Elder La., Decatur, IL (US) 62522; Hungming J. Liaw, 1013 Galen Dr., Champaign, IL (US) 61821; John Eddington, 36 Norwood Dr., Decatur, IL (US) 62521-4137; Yueqin Yang, 4661 Willow Brook La., Decatur, IL (US) 62521

( * ) Notice: Subject to any disclaimer, the term of this patent is extended or adjusted under 35 U.S.C. 154(b) by 0 days.

(21) Appl. No.: 09/290,234

(22) Filed: Apr. 13, 1999

Related U.S. Application Data

(62) Division of application No. 08/893,598, filed on Jul. 11, 1997, now Pat. No. 5,989,891, which is a division of application No. 08/740,066, filed on Oct. 24, 1996, now Pat. No. 5,834,231.

(51) Int. Cl.[7] ....................................................... C12P 7/60
(52) U.S. Cl. ........................ 435/138; 435/126; 435/136; 435/139; 435/252.1
(58) Field of Search ................................... 435/126, 136, 435/138, 139, 252.1

(56) References Cited

U.S. PATENT DOCUMENTS

| | | | |
|---|---|---|---|
| 3,043,749 | 7/1962 | Huang | 195/47 |
| 3,234,105 | 2/1966 | Motizuki et al. | 195/49 |
| 3,907,639 | 9/1975 | Makover et al. | 195/36 |
| 3,912,592 | 10/1975 | Makover et al. | 195/31 |
| 4,877,735 | 10/1989 | Nogami et al. | 435/138 |
| 4,892,823 | 1/1990 | Imai et al. | 435/138 |
| 4,933,289 | 6/1990 | Imai et al. | 435/253.3 |
| 4,935,359 | 6/1990 | Yin et al. | 435/138 |
| 4,945,048 | 7/1990 | Uchihori et al. | 435/105 |
| 4,960,695 | 10/1990 | Hoshino et al. | 435/42 |
| 5,082,785 | * 1/1992 | Manning et al. | 435/252.3 |
| 5,312,741 | 5/1994 | Hoshino et al. | 435/42 |
| 5,437,989 | 8/1995 | Asakura et al. | 435/190 |
| 5,474,924 | 12/1995 | Nogami et al. | 435/138 |
| 5,541,108 | 7/1996 | Fujiwara et al. | 435/252.1 |

FOREIGN PATENT DOCUMENTS

| | | |
|---|---|---|
| 1081470 | 2/1994 | (CN) . |
| 0 213 591 | 3/1987 | (EP) . |
| 0 221 707 | 5/1987 | (EP) . |
| 0 278 447 | 8/1988 | (EP) . |
| 0 518 136 | 12/1992 | (EP) . |
| 159/66 | 1/1966 | (JP) . |
| 160/66 | 1/1966 | (JP) . |
| 5907/66 | 3/1966 | (JP) . |
| 51-40154 | 4/1976 | (JP) . |
| 7-67673 | 3/1995 | (JP) . |
| 7-250671 | 10/1995 | (JP) . |
| 526660 | 10/1976 | (SU) . |

OTHER PUBLICATIONS

Derwent Computer Abstract 2000–303046 D'Elia Et Al WO200015827, Apr. 2000.*
Kieslich, K., vol. ed., "Biotransformations," *Biotechnology 6A*:436–437 (1934), Verlag Chemie, Weinhiem, Germany.
Martin, C.K. and Perlman, D., "Conversion of L–Sorbose to 2–Keto–L–Gulonic Acid By Mixtures of Immobilized Cells of *Gluconobacter melanogenus* IFO 3293 and *Pseudomonas* Species," *Eur. J. Appl. Microbiol.* 3:91–95 (1976).
Tsukada, Y. and Perlman, D., "The Fermentation of l–Sorbose by *Gluconobacter melanogenus*: General Characteristics of the Fermentation," *Biotechnology and Bioengineering XIV*:7999–810 (1972).
Walker, J.M. and Gingold, E.B., *Molecular Biology and Biotechnology*, The Royal Society of Chemistry, London, pp. 15–20 (1989).
Yin, G.–L. et al., "Studies on the Production of Vitamine C Precursor 2–Keto–L–Gulonic Acid from L–Sorbose by Fermentation. I. Isolation, Screening and Identification of 2–Keto–L–Gulonic Acid Producing Bacteria," *Acta Microbiologica Sinica* 20:246–251 (1980).
Yin, G.–L. et al., "Studies on Production of Vitamin C Precursor 2–Keto–L–Gulonic Acid from L–Sorbose by Fermentation," *Acta Microbiologica Sinica* 21:185–191 (1981).
Abstract of AP1, Derwent World Patents Index, WPI Account No. 77–48308Y/27, Oct. 31, 1976.
Abstract of AN2, Derwent World Patents Index, WPI Account No. 95–155907/21, Aug. 17, 1988.

* cited by examiner

*Primary Examiner*—Herbert J. Lilling

(57) ABSTRACT

The present invention relates to a process for the production of 2-keto-L-gulonic acid by fermentative conversion of L-sorbose and/or D-sorbitol. The present invention further relates to novel bacterial strains useful in this process.

1 Claim, 1 Drawing Sheet

BACTERIAL STRAINS AND USE THEREOF IN FERMENTATION PROCESSES FOR 2-KETO-L-GULONIC ACID PROTECTION

CONTINUING DATA AS CLAIMED BY APPLICANT

This application is a divisional of prior U.S. application Ser. No. 08/893,598, filed Jul. 11, 1997, now U.S. Pat. No. 5,989,891, which is a divisional of prior U.S. application Ser. No. 08/740,066, filed Oct. 24, 1996, now U.S. Pat. No. 5,834,231.

FIELD OF THE INVENTION

The present invention relates to a process for the production of 2-keto-L-gulonic acid by fermentative conversion of L-sorbose and/or D-sorbitol. The present invention further relates to novel bacterial strains useful in this process.

BACKGROUND OF THE INVENTION

2-Keto-L-gulonic acid ("2-KLG") is a significant intermediate in the preparation of L-ascorbic acid (vitamin C), an essential nutrient. 2-KLG has been synthesized in the past on an industrial scale using the Reichstein method (*Helvetica Chimica Acta* 17:311 (1934)). This method, however, has a number of disadvantages for commercial application, including the use of large quantities of solvents and the involvement of a number of complex reaction steps.

Accordingly, as an alternative to the Reichstein method, a number of processes employing one or more microorganisms have been developed to produce 2-KLG by fermentation. U.S. Pat. No. 2,421,611, for example, discloses a method involving microbial oxidation of D-glucose to 5-keto-D-gluconic acid, followed by chemical or microbial reduction to L-idonic acid and subsequent microbial oxidation to 2-KLG. Japanese Patent Publication Nos. 39-14493, 53-25033, 56-15877 and 59-35290, for example, disclose similar processes involving the microbial oxidation of D-glucose to 2,5-diketo-D-gluconic acid followed by microbial or chemical reduction to 2-KLG.

These methods, however, also suffer from a number of disadvantages that reduce their usefulness in commercial production of 2-KLG. For example, the chemical reduction steps in these methods (i.e. the reduction of 5-keto-D-gluconic acid to L-idonic acid and 2,5-diketo-D-gluconic acid to 2-KLG) are accompanied by problems with controlling the stereochemistry of reduction (thus producing D-gluconic acid and 2-keto-D-gluconic acid, respectively, as byproducts) which, in turn, reduces the yield of 2-KLG. Alternatively, when this reduction is performed by one or more microorganisms, excess sugar is required to provide an energy source for the reduction, which also reduces the yield of 2-KLG.

In view of these problems, an alternate pathway has been employed for the fermentative production of 2-KLG, which involves only oxidation of L-sorbose to 2-KLG via a sorbosone intermediate. A number of processes have been developed using this pathway that employ a wide range of microorganisms from the genera Gluconobacter, such as *Gluconobacter oxydans* (U.S. Pat. Nos. 4,935,359; 4,960,695; 5,312,741; and 5,541,108), Pseudogluconobacter, such as *Pseudogluconobacter saccharoketogenes* (U.S. Pat. Nos. 4,877,735; European Pat. No. 221 707), Pseudomonas, such as *Pseudomonas sorbosoxidans* (U.S. Pat. Nos. 4,933,289 and 4,892,823), and mixtures of microorganisms from these and other genera, such as Acetobacter, Bacillus, Serratia, Mycobacterium, and Streptomyces (U.S. Pat. Nos. 3,912,592; 3,907,639; and 3,234,105).

These processes, however, suffer from certain disadvantages that limit their usefulness for commercial production of 2-KLG. For example, the processes referenced above that employ *G. oxydans* also require the presence of an additional "helper" microbial strain, such as *Bacillus megaterium*, or commercially unattractive quantities of yeast or growth components derived from yeast in order to produce sufficiently high levels of 2-KLG for commercial use. Similarly, the processes that employ Pseudogluconobacter can require medium supplemented with expensive and unusual rare earth salts or the presence of a helper strain, such as *B. megaterium*, and/or the presence of yeast in order to achieve commercially suitable 2-KLG concentrations and efficient use of sorbose substrate. Other processes that employ *Pseudomonas sorbosoxidans* also include commercially unattractive qualities of yeast or yeast extract in the medium.

Accordingly, there is a need in the art for microorganism strains which efficiently produce 2-KLG, but without many of the problems associated with the state of the art.

SUMMARY OF THE INVENTION

It is therefore an object of the present invention to provide microorganism strains which efficiently produce 2-KLG. Other objects, features and advantages of the present invention will be set forth in the detailed description of preferred embodiments that follows, and in part will be apparent from the description or may be learned by practice of the invention. These objects and advantages of the invention will be realized and attained by the methods particularly pointed out in the written description and claims hereof.

These and other objects are accomplished by the methods of the present invention, which, in a first embodiment, is directed to a process for producing 2-KLG from L-sorbose, which comprises the steps of culturing in a medium a microorganism of strain NRRL B-21627 (ADM X6L) or a mutant or variant thereof, either alone or in mixed culture with one or more helper strains, and then recovering the accumulated 2-KLG. Another embodiment of the present invention is directed to a culture of a microorganism of strain NRRL B-21627 or a mutant thereof, such as NRRL B-21630 (ADM 86-96).

It is to be understood that both the foregoing general description and the following detailed description are exemplary and explanatory only and are intended to provide further explanation of the invention as claimed.

DETAILED DESCRIPTION OF PREFERRED EMBODIMENTS OF THE INVENTION

Figure 1:
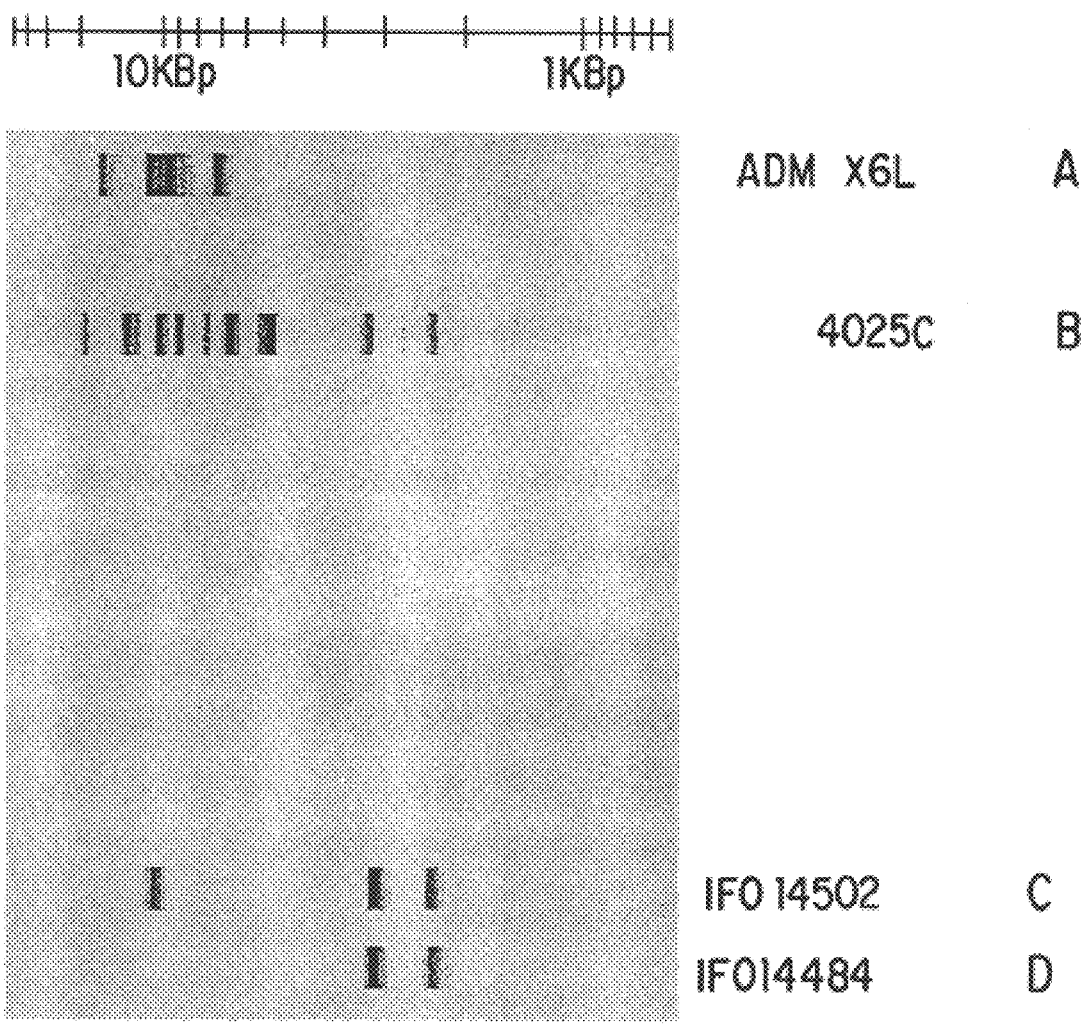
FIG. 1 is a depiction of the RiboPrint® patterns of bacterial strains capable of producing 2-KLG from L-sorbose. RiboPrint® pattern (A) was obtained from bacterial strain NRRL B-21627 (ADM X6L); RiboPrint® pattern (B) was obtained from *Gluconobacter oxydans* strain 4025C (a reisolate of the small-colony component strain of the mixed culture deposit DSM 4027, U.S. Pat. No. 4,935,359); RiboPrint® pattern (C) was obtained from *Pseudomonas sorbosoxidans* strain IFO 14502; and RiboPrint® pattern (D) was obtained from *Pseudogluconobacter saccharoketogenes* strain IFO 14484.

In a first embodiment, the present invention is directed to a fermentation process for the production of 2-keto-L- gulonic acid from L-sorbose which comprises contacting a microorganism with L-sorbose for a sufficient time and then isolating the accumulated 2-KLG. Preferably, the inventive fermentation process comprises cultivating a microorganism in a synthetic or natural culture medium containing L-sorbose for a sufficient time and then isolating the accumulated 2-KLG from the culture medium and/or cells of the microorganism.

The microorganism strain employed in the inventive process is preferably bacterial strain NRRL B-21627 (ADM X6L) or a mutant or variant thereof, which is capable of producing at least about 40 g/L of 2-KLG from L-sorbose by fermentation in pure culture, i.e., in the absence of one or more additional microorganism strain(s).

Strain NRRL B-21627 (ADM X6L) was deposited at the Agricultural Research Service Culture Collection (NRRL), 1815 North University Street, Peoria, Ill. 61604, USA, on Oct. 1, 1996 under the provisions of the Budapest Treaty and assigned accession number NRRL B-21627. The characteristics of strain NRRL B-21627 (ADM X6L) include:

(1) Cell Morphology—gram-negative; can be gram variable in older cultures; pleiomorphic; short rods or coccobacilli; cells appear singly and in pairs; can form short chains or filaments; does not form spores;

(2) Colony Morphology—punctiform, convex, entire, smooth, butyrous and translucent; beige or light brown coloration in older colonies on some media;

(3) Motility: no motility observed in wet mounts prepared from liquid cultures or 2% agar plate cultures; motility observed by stabbing fresh culture into a plate of BUGM™ medium (available from Biolog, Inc., Cat.#70001) that has been partially solidified using 0.3% to 0.4% agar; cells manufacture flagella under conditions used to observe motility;

(4) Temperature range: no growth observed at 4° C., 37° C. or 41 ° C., while good growth observed at 25° C. and 30° C.;

(5) pH range: no growth observed at pH 4.5; growth observed at pH 6.2; good growth observed at pH 7.2;

(6) Physiological characteristics:
  (a) catalase: positive;
  (b) oxidase: positive
  (c) gelatinase: negative;
  (d) aerobic, no growth under anaerobic conditions;
  (e) brown pigment formed from fructose;
  (f) acid is produced from ethanol;
  (g) dihydroxyacetone is not produced from glycerol;
  (h) does not form pellicle or ring within 24 hours in standing glucose or mannitol broth culture at pH in range of 4.0–5.0; and
  (i) sensitive to streptomycin; and (7) Cultural Characteristics:
  (a) growth in 3% NaCl: positive;
  (b) peptone-yeast extract-mannitol agar: growth;
  (c) Marine agar: slow growth;
  (d) BUGM™ and BUGM-G™: growth; and
  (e) Brain Heart Infusion agar: growth.

(8) RiboPrint® Analysis:
  RiboPrint® analysis involves hybridization of radio-labeled anti-sense RNA to the genetic material being studied, followed by detection of the labeled double-stranded hybrid using gel electrophoresis. The patterns obtained by this method are useful for differentiating not only between organisms of different species, but also between different strains of the same species. RiboPrint® patterns obtained for strain NRRL B-21627 (ADM X6L) and a number of comparative strains known to be capable of producing 2-KLG from L-sorbose are depicted in FIG. 1.

In addition to naturally occurring strain NRRL B-21627 (ADM X6L), mutants and variants thereof may also be employed in the inventive process, provided that these mutants and variants are also capable of producing at least 40 g/L of 2-KLG from L-sorbose in monoculture.

Illustrative examples of suitable methods for preparing mutants and variants of the inventive microorganism strains include, but are not limited to: mutagenesis by irradiation with ultraviolet light or X-rays, or by treatment with a chemical mutagen such as nitrosoguanidine (N-methyl-N'-nitro-N-nitrosoguanidine), methylmethanesulfonate, nitrogen mustard and the like; gene integration techniques, such as those mediated by insertional elements or transposons or by homologous recombination of transforming linear or circular DNA molecules; and transduction mediated by bacteriophages such as P1. These methods are well known in the art and are described, for example, in J. H. Miller, *Experiments in Molecular Genetics,* Cold Spring Harbor Laboratory Press, Cold Spring Harbor, N.Y. (1972); J. H. Miller, *A Short Course in Bacterial Genetics,* Cold Spring Harbor Laboratory Press, Cold Spring Harbor, N.Y. (1992); M. Singer and P. Berg, *Genes & Genomes,* University Science Books, Mill Valley, Calif. (1991); J. Sambrook, E. F. Fritsch and T. Maniatis, *Molecular Cloning: A Laboratory Manual,* 2d ed., Cold Spring Harbor Laboratory Press, Cold Spring Harbor, N.Y. (1989); P. B. Kaufman et al., *Handbook of Molecular and Cellular Methods in Biology and Medicine,* CRC Press, Boca Raton, Fla. (1995); *Methods in Plant Molecular Biology and Biotechnology,* B. R. Glick and J. E. Thompson, eds., CRC Press, Boca Raton, Fla. (1993); and P. F. Smith-Keary, *Molecular Genetics of Escherichia coli,* The Guilford Press, New York, N.Y. (1989).

Mutated strains derived from the inventive organism NRRL B-21627 (ADM X6L) using known methods are then preferably selected or screened for improved 2-KLG production potential or for other desirable properties related to their utility in producing 2-KLG from L-sorbose. In a particularly preferred embodiment of the mutagenesis and screening approach to strain improvement, mutagenized cells are selected on the basis of their resistance to growth-inhibitory concentrations of partially derivatized or degraded 2-KLG, such as 2-KLG derivatives generated by autoclaving or other exposure to heat. In an alternative embodiment, the selective agent may be generated by other means of chemical modification of 2-KLG, including, but not limited to: amino-substitution to create 2-amino-L-gulonic acid or 2-amino-L-idonic acid; oxidation at the $C_6$ position to create 5-keto-glucaric acid; modifications leading to various thiol- or deoxy-derivatives or various unsaturated derivatives of 2-KLG; or by any other means that will be clear to individuals versed in the art.

A particularly preferred mutant (ADM 86-96) of strain NRRL B-21627 (ADM X6L) was deposited at the Agricultural Research Service Culture Collection (NRRL), 1815 North University Street, Peoria, Ill. 61604, USA, on Oct. 15, 1996 under the provisions of the Budapest Treaty and assigned accession number NRRL B-21630.

In accordance with the present invention, the inventive microorganism strain or a mutant or variant thereof is contacted with L-sorbose for a sufficient time and then the accumulated 2-KLG is isolated. Preferably, the microorganism strain is cultivated in a natural or synthetic medium containing L-sorbose for a period of time for 2-KLG to be produced and the accumulated 2-KLG is subsequently isolated. Alternatively, a preparation derived from the cells of the microorganism strain may be contacted with L-sorbose for a sufficient time and the accumulated 2-KLG may then be isolated.

As used herein, "a preparation derived from the cells" is intended to mean any and all extracts of cells from the culture broths of the inventive strain or a mutant or variant thereof, acetone dried cells, immobilized cells on supports, such as polyacrylamide gel, κ-carrageenan and the like, and similar preparations.

An illustrative example of such a procedure involves adding L-sorbose and $CaCO_3$ in a suitable aqueous buffer, such as 2-(N-methylmorpholino)ethanesulfonic acid (pH 6.5; 0.5 M), to an aqueous extract of the microorganism strain in a shaker flask. This reaction preferably proceeds at a pH in the range of 5.0 to 8.0 at a temperature in the range of 20° C. to 40° C. for about 1 to 100 hours. The concentration of L-sorbose should be about 0.1 to 10% w/v, more preferably about 0.3 to 6% (w/v) and the amount of the preparation derived from the cells of strain NRRL B-21627 (ADM X6L) or a mutant or variant thereof, such as NRRL B-21630 (ADM 86-96), should be about 1 to 30 mg/ml. After shaking for a sufficient period of time under temperature and pH conditions empirically determined to maximize 2-KLG yield, the accumulated 2-KLG may be isolated by conventional methods.

The medium used herein may be solid or liquid, synthetic (i.e. man-made) or natural, and contains sufficient nutrients for the cultivation of the inventive microorganism strain. Preferably, the medium employed is a liquid medium, more preferably a synthetic liquid medium.

In the various embodiments of the process of the present invention, the starting material, L-sorbose, may be present in the medium prior to introduction of the inventive microorganism strain or may be added to the medium after introduction of the strain, either all at once at the beginning or continuously or in installments over the course of cultivation, or may be generated in situ by fermentative conversion of D-sorbitol. The amount of L-sorbose employed may be determined empirically by one skilled in the art, but is at least sufficient for the microorganism strain to produce at least about 40 g/L of 2-KLG. Preferably, L-sorbose comprises from 3 to 30% (w/v) of the culture medium, more preferably from 5 to 20%.

In a preferred embodiment of the present invention, the L-sorbose starting material is generated in situ by fermentative conversion of D-sorbitol using a suitable microorganism or mixture of microorganisms. Any microorganism or mixture of microorganisms that can convert D-sorbitol to L-sorbose in the presence of NRRL B-21627 (ADM X6L) or a mutant or variant thereof while not adversely affecting its ability to convert L-sorbose to 2-KLG may be employed. Preferably, the microorganism employed is a strain of *Gluconobacter oxydans*, more preferably *G. oxydans* strain ATCC 621 or *G. oxydans* strain IFO 3293. According to this preferred embodiment of the present invention, the D-sorbitol starting material may be present in the medium prior to introduction of one or more of the microorganisms or may be added to the medium after introduction of one or more of the microorganisms, either all at once at the beginning or continuously or in installments over the course of cultivation.

In addition to L-sorbose and/or D-sorbitol, the natural or synthetic culture medium also contains a nitrogen source, suitable inorganic salts, and, as appropriate, various trace nutrients, growth factors and the like suitable for cultivation of the microorganism strain, and may also contain at least one supplementary carbon source. The amount of each of these additional ingredients to be employed is preferably selected to maximize 2-KLG production. Such amounts may be determined empirically by one skilled in the art according to the various methods and techniques known in the art. In a particularly preferred embodiment of the present invention, the culture medium contains about 10% (w/v) of L-sorbose, about 3% (wt. dry solids/v) of corn steep liquor, and about 0.2% (w/v) of $MgSO_4.7H_2O$, with pH controlled using $NH_4OH$, $Ca(OH_2)$ or $CaCO_3$. Medium for use in preparing inoculum may contain additional components as appropriate, such as peptone or N-Z Amine, supplemental carbon sources and/or various vitamins.

Illustrative examples of suitable supplemental carbon sources include, but are not limited to: other carbohydrates, such as glucose, fructose, mannitol, starch or starch hydrolysate, cellulose hydrolysate and molasses; organic acids, such as acetic acid, propionic acid, lactic acid, formic acid, malic acid, citric acid, and fumaric acid; and alcohols, such as glycerol.

Illustrative examples of suitable nitrogen sources include, but are not limited to: ammonia, including ammonia gas and aqueous ammonia; ammonium salts of inorganic or organic acids, such as ammonium chloride, ammonium nitrate, ammonium phosphate, ammonium sulfate and ammonium acetate; urea; nitrate or nitrite salts, and other nitrogen-containing materials, including amino acids as either pure or crude preparations, meat extract, peptone, fish meal, fish hydrolysate, corn steep liquor, casein hydrolysate, soybean cake hydrolysate, yeast extract, dried yeast, ethanol-yeast distillate, soybean flour, cottonseed meal, and the like.

Illustrative examples of suitable inorganic salts include, but are not limited to: salts of potassium, calcium, sodium, magnesium, manganese, iron, cobalt, zinc, copper and other trace elements, and phosphoric acid.

Illustrative examples of appropriate trace nutrients, growth factors, and the like include, but are not limited to: coenzyme A, pantothenic acid, biotin, thiamine, riboflavin, flavine mononucleotide, flavine adenine dinucleotide, other vitamins, amino acids such as cysteine, sodium thiosulfate, p-aminobenzoic acid, niacinamide, and the like, either as pure or partially purified chemical compounds or as present in natural materials. Cultivation of the inventive microorganism strain may be accomplished using any of the submerged fermentation techniques known to those skilled in the art, such as airlift, traditional sparged-agitated designs, or in shaking culture.

The culture conditions employed, including temperature, pH, aeration rate, agitation rate, culture duration, and the like, may be determined empirically by one of skill in the art to maximize 2-KLG production. The selection of specific culture conditions depends upon factors such as the particular inventive microorganism strain employed, medium composition and type, culture technique, and similar considerations. In a particularly preferred embodiment of the present invention when employing strain NRRL B-21627 (ADM X6L) or a mutant or variant thereof, such as NRRL B-21630 (ADM 86-96), cultivation takes place at a temperature in the range of 22° C. to 35° C., preferably about 30° C., and at a pH in the range of 5.0 to 8.0, preferably in the range of 5.5 to 7.5, more preferably about 6.0 to 6.8. The culture conditions employed can, of course, be varied by known methods at different timepoints during cultivation, as appropriate, to maximize 2-KLG production.

After cultivation for a sufficient period of time, such as, for example, from 10 to 150 hours, the 2-KLG that has accumulated in the cells and/or culture broth is isolated according to any of the known methods. Any method that is suitable with the conditions employed for cultivation may be used; illustrative examples of suitable methods for recovering 2-KLG are described in U.S. Pat. Nos. 5,474,924; 5,312,741; 4,960,695; 4,935,359; 4,877,735; 4,933,289; 4,892,823; 3,043,749; 3,912,592; 3,907,639 and 3,234,105.

According to one such method, the microorganisms are first removed from the culture broth by known methods, such as centrifugation or filtration, and the resulting solution concentrated in vacuo. Crystalline 2-KLG is then recovered by filtration and, if desired, purified by recrystallization. Similarly, 2-KLG can be recovered using such known methods as the use of ion-exchange resins, solvent extraction, precipitation, salting out and the like.

When 2-KLG is recovered as a free acid, it can be converted to a salt, as desired, with sodium, potassium, calcium, ammonium or similar cations using conventional methods. Alternatively, when 2-KLG is recovered as a salt, it can be converted to its free form or to a different salt using conventional methods.

In an alternative embodiment of the present invention, the inventive microorganism is cultivated in mixed culture with one or more helper strains. As used herein, "helper strain" is intended to mean a strain of a microorganism that increases the amount of 2-KLG produced in the inventive process. Suitable helper strains can be determined empirically by one skilled in the art. Illustrative examples of suitable helper strains include, but are not limited to, members of the following genera: Aureobacterium (preferably *A. liquefaciens* or *A. saperdae*), Corynebacterium (preferably *C. ammoniagenes* or *C. glutamicum*), Bacillus, Brevibacterium (preferably *B. linens* or *B. flavum*), Pseudomonas, Proteus, Enterobacter, Citrobacter, Erwinia, Xanthomonas and Flavobacterium. Preferably, the helper strain is *Corynebacterium glutamicum* ATCC 21544.

The helper strain is preferably incubated in an appropriate medium under suitable conditions for a sufficient amount of time until a culture of sufficient population is obtained. This helper strain inoculum may then be introduced into the culture medium for production of 2-KLG either separately or in combination with the inventive microorganism strain, i.e., a mixed inoculum. Preferably, the ratio of the amount of the helper strain relative to the amount of strain NRRL B-21627 (ADM X6L) is in the range of from 10:1 to 1:10,000.

Another embodiment of the present invention is directed to the novel microorganism strains described above which are useful in fermentation processes for the production of 2-KLG.

The following examples are illustrative only and are not intended to limit the scope of the invention as defined by the appended claims. It will be apparent to those skilled in the art that various modifications and variations can be made in the methods of the present invention without departing from the spirit and scope of the invention. Thus, it is intended that the present invention cover the modifications and variations of this invention provided they come within the scope of the appended claims and their equivalents.

All patents and publications referred to herein are expressly incorporated by reference.

EXAMPLES

Example 1

Isolation of Strain NRRL B-21627 (ADM x6L)

A. Origin, Enrichment and Screening for Soil Samples

Environmental specimens were subjected to microbial enrichment in shake flasks. The resulting mixed cultures were screened to identify those containing at least one microorganism strain capable of producing 2-KLG from L-sorbose. Samples of moist soil, sand, sediment, fruit, berries, humus, and other environmental specimens were collected from various regions of the U.S.A. Each specimen was immediately stored in a cool, ventilated, humidified container. Enrichments were started by adding one gram of soil or specimen to 30 mL of Medium A (Table 1) in a 250 mL baffled shake flask, followed by shaking incubation at 30° C., 230 rpm, for 49 hours.

To screen the enrichments by fermentation, 0.5 to 0.75 mL of each enrichment was transferred to a 250 mL baffled flask containing 30 mL of fresh Medium B (Table 1). These flasks were shaken at 30° C., 230 rpm for 68 hours, after which portions of the mixed culture fermentations were analyzed for 2-KLG content, and cryogenically preserved. For preservation, 2.0 mL of each culture was mixed with 1.0 mL of sterile 40% glycerol in water, then stored at −70° C.

Flasks were screened for 2-KLG production using thin layer chromatography on Whatman LK5 Silica Gel 150 plates, 250 mm thickness (Catalog No. 4855-820). The plates were spotted with 5 $\mu$L of centrifuged culture broth, and developed for 5–6 hours in solvent (157 mL of n-propanol; 39 mL of deionized water; 4 mL of 1% phosphoric acid; 0.4 mL of glacial acetic acid). The plates were air dried and then sprayed with 0.125 g of tetrazolium blue chloride dissolved in 25 mL of methanol and 25 mL of 6N sodium hydroxide, after which they were baked at 60° C. for 5 minutes. Sorbose and 2-KLG were visualized as purple spots on the finished plates, and were identified by comparison with a standard containing 10 gL each of 2-KLG and L-sorbose.

Production of 2-KLG was quantitated by HPLC. Samples were prepared by 1:10 dilution in mobile phase, followed by filtration through 0.45 $\mu$m porous membranes. Mobile phase contained 1.1 mL of ACS grade sulfuric acid diluted to 4.0 L using Milli-Q water. Samples of 100 $\mu$L each were loaded on two 2 mm×300mm×7.8 mm Aminex HPX-87H columns (BioRad) arranged in series to provide a total column length of 600 mm, preceded by a guard column of the same resin. The column was run at 55° C. using a flow rate of 0.6 mL/min. L-sorbose and 2-KLG were detected using a Waters Model No. 410 differential refractometer, and were identified by comparison to a standard containing 2-KLG and L-sorbose.

Thirty-three (33) of the mixed culture fermentations produced 2-KLG, in amounts ranging from 1.8 to 9.3 g/L. The mixed culture fermentation from soil sample #216B, from which strain NRRL B-21627 was later isolated (Example 1B), produced 6.3 g/L of 2-KLG.

B. Isolation and Testing of Monocultures

Pure cultures of microorganisms capable of producing 2-KLG from L-sorbose, either in monoculture or in mixed culture with other microorganisms, were isolated from the enrichments described above. Eleven mixed-culture enrichments from Example 1A were chosen on the basis of their superior 2-KLG production. These were thawed and diluted in 10-fold serial increments using Medium A, after which 0.1 mL of each dilution was spread on the surface of a Medium A agar plate. The plates were incubated at 30° C. for 24 hours, then examined under 8- to 40-fold magnification. Attention to the smallest, slowest-growing colonies was necessary in order to recover 2-KLG producing strains from the dilution plates. Several examples of each colony type and size were selected and subcultured on fresh Medium A plates, after which the dilution plates were returned to 30° C. for 24 hours. Additional slow-growing colonies were selected from the dilution plates and subcultured after the second incubation period. Each strain was streak-purified for 1–3 cycles on either Medium A plates or on PYM plates (10 g/L peptone; 10 g/L yeast extract; 0.5 g/L glycerol; 30 g/L mannitol; 20 g/L agar). The pure strains were cryogenically preserved at −70° C. in PYM liquid medium containing 20% glycerol. A total of 118 pure strains were recovered from the eleven enrichment mixtures.

The 118 new strains were tested for their potential to convert L-sorbose into 2-KLG in shake flasks. To account for the possibility that 2-KLG production might require the combined activity of two or more microorganisms, each new isolate was tested in pairwise combination with all other strains originating from the same enrichment, as well as in pure culture. To prepare inoculum, each strain was cultured on PYM agar for 24 hours, after which a large loop of cells was suspended in sterile buffer containing 50 mM sodium phosphate, 0.4% sodium chloride, and 0.05% mannitol, pH 7.2. For each pure-strain or paired-strain test, a 250 mL baffled flask containing thirty mL of Medium C (Table 1) was inoculated with 0.2 mL of cell suspension of each of the relevant strains. These flasks were shaken at 30° C., 230 rpm for 24 hours, after which 1.0 mL was transferred to 30 mL of fermentation Medium D (Table 1). The fermentation flasks were shaken at 30° C., 230 rpm for three days, then the broth was analyzed for 2-KLG and sorbose content using TLC and HPLC. 105 flasks were required to test the strains from soil sample #216B. Eighteen of these produced 2-KLG in amounts ranging from 1.9 to 19.3 g/L, fourteen of which had been inoculated with isolate ADM X6L (Table 2). The fact that strain ADM X6L (NRRL B-21627) made 14.9 g/L of 2-KLG in pure culture verified its identity as a 2-KLG producing strain.

TABLE 1

Media employed in Example 1

| Ingredient (g/L) | A | B | C | D |
|---|---|---|---|---|
| L-sorbose | 20.0 | 50.0 | 20.0 | 50.0 |
| D-glucose | 2.0 | 0.0 | 1.0 | 0.0 |
| Corn Steep Liquor dry solids | 10.0 | 10.0 | 15.0 | 15.0 |
| FeSO$_4$.H$_2$O | 0.1 | 0.1 | 0.1 | 0.1 |
| Yeast Nitrogen Base | 1.7 | 1.7 | 1.7 | 1.7 |
| CaCO$_3$ | 6.0 | 20.0 | 6.0 | 20.0 |
| Cycloheximide | 0.005 | 0.005 | 0.0 | 0.0 |

*The glucose, corn steep liquor, iron sulfate and calcium carbonate were adjusted to pH 7.9, then autoclaved for 20 minutes. The remaining ingredients were adjusted to pH 6.3, then sterilized by filtration. The finished medium had a pH in the range of 7.1–7.4. Yeast Nitrogen Base was Difco product #0335-15-9.

TABLE 2

2-KLG production by strain ADM X6L in pure culture and in mixed culture with other strains from soil sample #216-B

| 216-B strain combination | 2-KLG (g/L) | L-sorbose (g/L) | % conversion yield* |
|---|---|---|---|
| ADM X6L | 14.9 | 34.6 | 96.7 |
| ADM X6L + 1 | 3.1 | 2.3 | 6.5 |
| ADM X6L + 3 | 1.9 | 1.3 | 3.9 |
| ADM X6L + 4 | 11.6 | 33.2 | 69.0 |
| ADM X6L + 7 | 16.3 | 27.3 | 71.8 |
| ADM X6L + 10 | 19.2 | 26.2 | 80.7 |
| ADM X6L + 11a | 13.6 | 33.1 | 80.5 |
| ADM X6L + 11b | 18.5 | 27.6 | 82.6 |
| ADM X6L + 15 | 9.5 | 32.3 | 53.7 |
| ADM X6L + 16 | 8.2 | 31.0 | 43.1 |
| ADM X6L + 17 | 19.0 | 26.1 | 79.5 |
| ADM X6L + 18a | 19.3 | 24.8 | 76.6 |

TABLE 2-continued

2-KLG production by strain ADM X6L in pure culture and in mixed culture with other strains from soil sample #216-B

| 216-B strain combination | 2-KLG (g/L) | L-sorbose (g/L) | % conversion yield* |
|---|---|---|---|
| ADM X6L + 18b | 2.4 | 0.0 | 4.8 |
| ADM X6L + 19 | 14.1 | 29.0 | 67.1 |

*percent conversion yield refers to the weight percentage of consumed L-sorbose that was found as 2-KLG.

Example 2

Production of 2-KLG from L-Sorbose by Strain NRRL B-21627 in Shake Flasks

Strain NRRL B-21627 was cultured on BUGMυ solid agar medium at 30° C., then colonies were transferred with a sterilized toothpick to a 250 mL baffled shake flask containing 20 mL of Medium E (Table 3). The seed culture was incubated at 30° C., 240 rpm for 24 hours. Twenty mL of production medium (Medium F, Medium G or Medium H; Table 3) in a 250 mL baffled flask was then inoculated with 2 mL of this seed. The culture was incubated at 30° C., 240 rpm for 72 hours. The broth was subsequently withdrawn and analyzed by HPLC. The 2-KLG production results are shown in Table 4.

TABLE 3

Media employed in Example 2

| Ingredient (amount/liter) | E$^a$ | F$^b$ | G$^c$ | H$^b$ |
|---|---|---|---|---|
| Yeast extract | 10.0 g | 15 g | 0 | 0 |
| Glycerol | 5.0 mL | 0.5 mL | 0 | 5.0 mL |
| MgSO$_4$.7H$_2$O | 0 | 2.5 g | 2.5 g | 2.5 g |
| CaCO$_3$ | 0 | 25.0 g | 25.0 g | 25.0 g |
| L-sorbose | 0 | 87.5 g | 95.8 g | 81.3 g |
| Corn steep liquor dry solids | 0 | 0 | 20.0 g | 20.0 g |
| Bactopeptone | 10.0 g | 0 | 15.0 g | 0 |
| D-mannitol | 0 | 0 | 14.4 g | 0 |
| Niacinamide (5 g/L) | 0 | 0 | 9.6 mL | 0 |
| Thiamine | 0 | 0 | 0.028 g | 0 |
| Pantothenic acid | 0 | 0 | 0.383 g | 0 |
| p-aminobenzoic acid | 0 | 0 | 0.192 g | 0 |
| D-sorbitol | 20.0 g | 0 | 0 | 0 |

$^a$pH was adjusted to 7.0 prior to autoclaving for 20 minutes
$^b$L-sorbose was autoclaved for 20 minutes and then added to the remaining ingredients, which had first been adjusted to pH 7.2 and autoclaved for 20 minutes
$^c$vitamins were adjusted to pH 7.0 and sterilized by filtration, then added to the L-sorbose and D-mannitol, which had been autoclaved for 20 minutes. This mixture was then added to the remaining ingredients, which had first been adjusted to pH 7.2 and autoclaved for 20 minutes.

TABLE 4

2-KLG Production by NRRL B-21627 in Flasks

| MEDIUM | 2-KLG (g/L) |
|---|---|
| F | 18.6 |
| G | 35.6 |
| H | 27.1 |

Example 3

Comparsion of 2-KLG Production from L-Sorbose in Pure Culture by Strain NRRL B-21627 Relative to Other Strains The inventive microorganism strain NRRL B-21627 (ADM X6L) and *Gluconobacter oxydans* strain 4025C (a reisolate of the small-colony component strain of the mixed culture deposit DSM 4027, U.S. Pat. No. 4,935,359) were tested for production of 2-KLG from L-sorbose using several different media (Table 5) and protocols. The results (Table 6) showed significantly higher 2-KLG production by strain NRRL B-21627 in a variety of culture media. In addition, the two strains were affected differently by the switch from medium I/J to medium K/L.

TABLE 5

Media employed in Example 3

| Ingredient (amount/L) | I | J | K | L |
|---|---|---|---|---|
| N-Z Soy ™ (Sheffield) | 0 | 0 | 10.0 g | 0 |
| ADM Arcon F ™ (ADM Co.) | 0 | 0 | 0 | 10.0 g |
| Corn Steep Liquor (dry solids) | 20.0 g | 20.0 g | 20.0 g | 20.0 g |
| Bactopeptone (Difco) | 10.0 g | 15.0 g | 0 | 0 |
| L-sorbose | 0 | 100.0 g | 0 | 70.0 g |
| D-sorbitol | 10.0 g | 0 | 5.0 g | 4.8 g |
| D-mannitol | 10.0 g | 15.0 g | 10.0 g | 0 |
| niacinamide | 0 | 0.05 g | 0 | 0.048 g |
| thiamine | 0 | 0.3 g | 0 | 0.29 g |
| pantothenic acid | 0 | 0.4 g | 0 | 0.386 g |
| p-aminobenzoic acid | 0 | 0.2 g | 0 | 0.193 g |
| $MgSO_4 \cdot 7H_2O$ | 0 | 2.5 g | 0 | 2.0 g |
| $CaCO_3$ | 10.0 g | 25.0 g | 10.0 g | 25.0 g |
| pH (before autoclave) | 6.5 | 7.2 | 6.5 | 7.2 |

TABLE 6

Comparison of 2-KLG production by NRRL B-21627 and 4025C in pure culture shake flasks.

| | Seed Medium/Fermentation Medium | | |
|---|---|---|---|
| Strain | C/D[a] | I/J | K/L |
| B-21627 | 16.0[b] | 39.7 | 33.5 |
| 4025C | 5.4[b] | 17.8 | 19.0 |

[a]For media C/D (Table 1), the experimental protocol of Example 1B was used, except that the strains were initially cultured on BUGM ™ agar, not PYM agar. For media I/J and K/L (Table 5), the experimental protocol of Example 2 was used.
[b]2-KLG value for ADM X6L in C/D media is average of nine trials; for 4025C the value is average of six trials.

Example 4

Production of 2-KLG from L-Sorbose in Shake Flasks by Mixed Cultures Comprised of NRRL B-21627 and a Second Microorganism Baffled 250 mL shake flasks containing 20 mL of medium I were inoculated with 100 μL of a frozen culture of NRRL B-21627 and a like volume of a second strain. The flasks were shaken at 240 rpm, 30° C. for 24 hours. Two mL of this culture was then transferred to a 250 mL baffled flask containing 25 mL of medium M (Table 9). After 65 hours shaking at 240 rpm, 30° C., the flasks were analyzed by HPLC for formation of 2-KLG from L-sorbose. The results are shown in Table 7.

TABLE 7

Production of 2-KLG from L-sorbose by mixed cultures containing strain NRRL B-21627 (ADM X6L) in flasks.

| Producer culture | Helper culture* | 2-KLG g/L | yield %** |
|---|---|---|---|
| X6L | — | 28.3 | 100.0 |
| X6L | ATCC 19354 | 47.7 | 89.9 |
| X6L | ATCC 19391 | 42.4 | 82.5 |
| X6L | ATCC 21544 | 45.6 | 100.0 |
| X6L | ATCC 21529 | 41.7 | 96.1 |
| X6L | NRRL B-14840 | 41.2 | 81.3 |
| X6L | NRRL B-43647 | 35.6 | 83.4 |

*Strains ATCC 19354, ATCC 19391, ATCC 21544, ATCC 21529, NRRL B-14840, and NRRL B-43647 are Corynebacterium ammoniagenes, Brevibacterium linens, Corynebacterium glutamicum, Brevibacterium flavum, Aureobacterium saperdae, and Aureobacterium liquifaciens, respectively.
**yield % refers to the weight percentage of consumed L-sorbose that was found as 2-KLG.

Example 5

Mutagenesis, Screening and Selection for Improved Variants of Strain NRRL B-21627.

The inventive bacterial strain NRRL B-21627 (ADM X6L) and mutants thereof were subjected to mutagenesis, and variants showing improved 2-KLG production were recovered. Bacterial cultures were grown to mid-log phase in BUGM™ or PYM broth medium, then pelleted by centrifugation and resuspended in 2 mL of filter-sterilized TM buffer in a glass tube (Tris.HCl 6.0 g/L, maleic acid 5.8 g/L, $(NH_4)_2SO_4$ 1.0 g/L, $Ca(NO_3)_2$ 5.0 mg/L, $MgSO_4 \cdot 7H_2O$ 0.1 g/L, $FeSO_4 \cdot 7H_2O$ 0.25 mg/L, adjusted to pH 6.0 using KOH). The 2 mL cell suspension was mixed with 2.5 μL of a 5.0 mg/mL solution of N'-nitro-N-nitrosoguanidine (NTG), then incubated at 30° C. for 25 minutes. An untreated cell suspension was similarly incubated as a control for estimating kill rate. After incubation, 10 mL of TM buffer was added to each tube, then the cells were pelleted, washed twice in TM buffer, then resuspended in 4.0 mL of 0.1 M $NaH_2PO_4$ (phosphate buffer) adjusted to pH 7.2 using KOH. The washed cell suspensions were further diluted in phosphate buffer, and aliquots were spread on plates of BUGM™ or CM2 agar media then incubated at 30° C. (BUGM™ is available from Biolog, Inc., Cat.#70001; CM2 medium contained D-sorbitol 5.0 g/L, $(NH_4)_2SO_4$ 2.0 g/L, $K_2HPO_4$ 0.1 g/L, $KH_2PO_4$ 0.9 g/L, $FeCl_3 \cdot 6H2O$ 5 mg/L, $MnSO_4 \cdot 4H2O$ 5 mg/L, casamino acids 2.0 g/L, yeast extract 2.0 g/L, agar 15.0 g/L, pH adjusted to 7.0 prior to autoclaving; the following CM2 components were sterilized by filtration: $MgSO_4 \cdot 7H2O$ 0.25 g/L, thiamine.HCl 30 mg/L, pantothenic acid and niacinamide 10 mg/L, and p-aminobenzoic acid 5 mg/L). Relative to unmutagenized control cells, the kill rate from NTG treatment was 60% to 80%. Surviving colonies were picked at random and screened for improved 2-KLG production from L-sorbose in shake flasks. Alternatively, mutagenized cell suspensions were diluted and spread on plates of growth-inhibitory CM2-S selective agar medium (CM2-S is CM2 with 7–8% 2-KLG added to the heat-sterilizable components of the medium prior to autoclaving). Colonies that grew on CM2-S agar were picked and tested for improved potential to produce 2-KLG from L-sorbose in shake flasks.

A. Production of 2-KLG from L-Sorbose By NRRL B-21627 and Mutant Derivatives in Pure Culture Shaker Flask Fermentation For each tested strain, 0.1 mL of frozen culture was inoculated into a 250 mL baffled flask containing 20 mL seed medium K (Table 5), then incubated at 30° C. for 24 hours at 240 rpm. 2 mL of seed contents were used to inoculate 25 mL of fermentation medium M (Table 9) in a 250 mL baffled shaker flask, and the flasks were shaken for 72 hours at 30° C., 240 rpm. The 2-KLG product was assayed by HPLC (Table 8).

TABLE 8

2-KLG production from L-sorbose by pure cultures in shaker flasks.

| Strain | Type | 2-KLG (g/L) |
|---|---|---|
| X6L | wild type | 27.5 |
| 77-111 | mutant of X6L | 40.6 |
| 86-96* | 2-KLG-resistant mutant of 77-11 | 64.4 |

*Strain selected on CM2-S agar medium.

B: Production of 2-KLG from L-Sorbose By NRRL B-21627 and Mutant Derivatives in Pure Culture Fermentors For each strain, a 250 mL baffled flask containing 35 mL of seed medium N (Table 9) was inoculated with 0.2 mL of a frozen culture, then incubated at 30° C., 240 rpm for 24 hours. 35 mL seed contents were used to inoculate 700 mL of fermentation medium O (Table 9) in a 1.5 L Applikon fermentor. The fermentation was conducted for 72 hours under the following controlled conditions: 32° C., 1000 rpm, pH 6.3 adjusted using 21% $NH_4OH$, aeration of 1500 mL/min. The 2-KLG product was assayed by HPLC (Table 10).

TABLE 9

Media employed in Examples 4 and 5

| Ingredient (amount/L) | M | N | O |
|---|---|---|---|
| N-Z Soy ™ (Sheffield) | 10.0 g | 5.0 g | 10.0 g |
| Corn Steep Liquor (dry solids) | 20.0 g | 10.0 g | 20.0 g |
| L-sorbose | 70.0 g | 0 | 70.0 g |
| D-sorbitol | 4.2 g | 5.0 g | 5.0 g |
| niacinamide | 0.04 g | 0 | 0.05 g |
| thiamine | 0.25 g | 0 | 0.3 g |
| pantothenic acid | 0.34 g | 0 | 0.4 g |
| p-aminobenzoic acid | 0.168 g | 0 | 0.2 g |
| $MgSO_4 \cdot 7H_2O$ | 2.0 g | 0 | 2.0 g |
| $CaCO_3$ | 25.0 g | 5.0 g | 25.0 g |
| Antifoam 6000K | 0 | 0 | 0.4 mL |
| pH (before autoclave) | 7.2 | 6.5 | 7.2 |

TABLE 10

2-KLG production from L-sorbose by pure cultures in fermentors.

| Strain | Type | 2-KLG (g/L) | molar yield % |
|---|---|---|---|
| X6L | wild type | 65 | 84 |
| 54-164 | mutant of X6L | 72.2 | 84 |
| 64-165 | mutant of X6L | 76.3 | 82 |
| 65-93 | mutant of X6L | 76 | 94 |
| 66-44 | mutant of X6L | 73.5 | 87 |
| 66-53 | mutant of X6L | 74.8 | 83 |

*molar yield % refers to the molar percentage of consumed L-sorbose that was found as 2-KLG.

Example 6

2-KLG Production from D-Sorbitol in Fermentors by Mixed Cultures Comprised of ADM 86-96 (NRRL B-21630) and a Second Microorganism Strain ADM 86-96 (NRRL B-21630), a mutant variant of NRRL B-21627, was cultured in the presence of a second microorganism having the capability of converting D-sorbitol to L-sorbose. A 500 mL baffled flask containing 50 mL of seed medium P (Table 12) was inoculated with 0.2 mL of frozen culture of strain ADM 86-96 and a like volume of either ADM 29-121 (a mutant of strain IFO 3293) or ATCC 621 as the second microorganism. The flasks were shaken at 240 rpm, 30° C. for 24 hr. Seed contents were used to inoculate 700 mL of fermentation medium Q (Table 12) in a 1.5 L Applikon fermentor. The fermentation was conducted for 43–70 hours under the following conditions: 30° C., 800 rpm of agitation, 1.8 VVM of aeration, pH maintained at 6.0 using 17% $NH_4OH$. The results are shown in Table 11.

TABLE 11

2-KLG production from D-sorbitol by mixed-strain cultures in fermentors.

| L-sorbose producing strain | 2-KLG (g/L) producing strain | 2-KLG (g/L) | % Conversion Yield* |
|---|---|---|---|
| ADM 29-121 (mutant of IFO 3293) | 86-96 | 109 | 96 |
| ATCC 621 | 86-9 | 114 | 98 |

*g 2-KLG produced/(g D-sorbitol − g residual L-sorbose)

TABLE 12

Media employed in Example 6

| Ingredient (amount/L) | P | Q |
|---|---|---|
| N-Z Soy ™ (Sheffield) | 10.0 g | 0 |
| Corn Steep Liquor (dry solids) | 20.0 g | 31.5 g |
| D-sorbitol | 10.0 g | 105.0 g |
| D-mannitol | 20.0 g | 0 |
| niacinamide | 0.05 g | 0 |
| thiamine | 0.3 g | 0 |
| pantothenic acid | 0.4 g | 0 |
| p-aminobenzoic acid | 0.2 g | 0 |
| $MgSO_4 \cdot 7H_2O$ | 0 | 2.0 g |
| $CaCO_3$ | 10.0 g | 25.0 g |
| Antifoam 6000K | 0 | 0.4 mL |
| pH (before autoclave) | 6.5 | 7.2 |

What is claimed is:

1. A process for the production of 2-keto-L-gulonic acid, which comprises culturing a microorganism strain in a medium containing L-sorbose for a time sufficient for said L-sorbose to be converted to 2-keto-L-gulonic acid; and recovering said 2-keto-L-gulonic acid; wherein said microorganism strain is prepared by transforming microorganism strain NRRL B-21267 or a mutant thereof with linear or circular DNA molecules.

* * * * *